(12) United States Patent
Nakayama (10) Patent No.: US 7,561,667 B2
(45) Date of Patent: Jul. 14, 2009

(54) RADIATION IMAGE CAPTURING APPARATUS, METHOD OF CONTROLLING SAME, APPARATUS FOR AND METHOD OF ADJUSTING RADIATION DOSE DETECTOR

(75) Inventor: Hiroki Nakayama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 88 days.

(21) Appl. No.: 11/865,029

(22) Filed: Sep. 30, 2007

(65) Prior Publication Data

US 2008/0080671 A1    Apr. 3, 2008

(30) Foreign Application Priority Data

Sep. 29, 2006    (JP)    .............................. 2006-269566

(51) Int. Cl.
*H05G 1/44*    (2006.01)
(52) U.S. Cl. ............................. 378/97; 378/108; 378/37
(58) Field of Classification Search ................... 378/16, 378/37, 97, 98.7, 108, 117
See application file for complete search history.

(56) References Cited

U.S. PATENT DOCUMENTS

| | | | | |
|---|---|---|---|---|
| 4,160,906 A | * | 7/1979 | Daniels et al. ................. | 378/97 |
| RE33,634 E | * | 7/1991 | Yanaki ........................ | 378/110 |
| 5,751,783 A | * | 5/1998 | Granfors et al. .............. | 378/108 |
| 6,047,042 A | * | 4/2000 | Khutoryansky et al. ........ | 378/62 |
| 6,151,383 A | * | 11/2000 | Xue et al. .................... | 378/108 |
| 6,556,655 B1 | * | 4/2003 | Chichereau et al. .......... | 378/108 |
| 7,133,490 B2 | * | 11/2006 | Muller et al. ................. | 378/37 |
| 7,431,500 B2 | * | 10/2008 | Deych et al. ................ | 378/207 |

FOREIGN PATENT DOCUMENTS

| | | |
|---|---|---|
| EP | 1 004 875 A2 | 5/2000 |
| JP | 2000-197624 A | 7/2000 |
| JP | 2004-154409 A | 6/2004 |

* cited by examiner

*Primary Examiner*—Edward J Glick
*Assistant Examiner*—Thomas R Artman
(74) *Attorney, Agent, or Firm*—Sughrue Mion, PLLC (57) ABSTRACT

A radiation image capturing apparatus is capable of setting highly accurately an optimum dose of radiation to be applied to an area of interest of a subject. A solid-state detector acquires radiation image information of a breast from a radiation that has been emitted from a radiation source and passed through the breast. A detected value is compared with a predetermined threshold value used to identify the area of interest, and a detection corrective value is calculated based on detected values from the region including the area of interest and detected values from the area of interest. Based on the detection corrective value, an AEC corrector corrects a radiation dose detected by an identified one of AEC sensors, and an exposure control condition depending on the area of interest to be imaged of the subject is determined based on the corrected radiation dose.

20 Claims, 6 Drawing Sheets

RADIATION IMAGE CAPTURING APPARATUS, METHOD OF CONTROLLING SAME, APPARATUS FOR AND METHOD OF ADJUSTING RADIATION DOSE DETECTOR

BACKGROUND OF THE INVENTION

1. Field of the Invention

The present invention relates to a radiation image capturing apparatus for capturing the radiation image information of a subject using a radiation dose detector for detecting a radiation dose that has passed through the subject, a method of controlling such a radiation image capturing apparatus, an apparatus for and a method of adjusting a radiation dose detector.

2. Description of the Related Art

In the medical field, there have widely been used radiation image capturing apparatus which apply a radiation emitted from a radiation source to a subject and guide the radiation that has passed through the subject to a solid-state detector to detect the radiation, for thereby recording radiation image information of the subject.

The solid-state detector includes a solid-state detecting unit comprising a matrix of charge collecting electrodes formed on an insulating substrate and a radiation conductor disposed on the charge collecting electrodes for generating electric charges depending on the radiation that is applied to the solid-state detecting unit. The electric charges generated by the radiation conductor as representing radiation image information are collected by the charge collecting electrodes and temporarily stored in an electric storage unit. The collected electric charges are converted into an electric signal, which is output from the solid-state detector.

One known radiation image capturing apparatus is a mammographic system used for breast cancer screening. The mammographic system comprises an image capturing base housing a panel-like solid-state detector for supporting a subject's breast, a presser plate disposed in confronting relation to the image capturing base for pressing the breast against the image capturing base, and a radiation source for applying a radiation through the presser plate to the breast.

The subject's breast comprises a mammary gland region and a fat region. In terms of breast cancer screening, the area of interest is the mammary gland region because it is highly susceptible to breast cancer. While the mammary gland region has a large coefficient of absorption of radiations, the fat region has a small coefficient of absorption of radiations and absorbs almost no radiations (see Japanese laid-open patent publication No. 2000-197624).

In order to acquire appropriate radiation image information of the mammary gland region, it is necessary to set suitable exposure control conditions based on the mammary gland region for applying a desired dose of radiation to the mammary gland region. The exposure control conditions include a tube voltage, a tube current, a radiation exposure time, etc. to be established for the radiation source. Of these exposure control conditions, the tube current and the radiation exposure time are the most important conditions for determining a dose of radiation to be applied to the subject. The position of the mammary gland region varies from individual to individual and differs according to various factors including body type, age, etc. The radiological technician estimates the position of the mammary gland of the subject based on the findings of the breast to be diagnosed, determines a position for a radiation dose detecting sensor with respect to the breast, and moves the radiation dose detecting sensor to the determined position. Therefore, as the experience and skill of the radiological technician plays an important role in determining a best position for the radiation dose detecting sensor, appropriate radiation image information of the mammary gland regions of various subjects may not stably be obtained. It is a complex task to move the radiation dose detecting sensor because it is manually moved by the radiological technician.

The radiation dose detecting sensor includes a light-detecting surface having a certain area. Insofar as the mammary gland region to be imaged covers the entire light-detecting surface of the radiation dose detecting sensor, a detected value from the radiation dose detecting sensor properly represents the dose of the radiation that has passed through the mammary gland region.

However, if the mammary gland region to be imaged covers only a portion of the entire light-detecting surface, then a detected value from the radiation dose detecting sensor represents the sum of the dose of the radiation that has passed through part of the mammary gland region and the dose of the radiation that has passed through part of the fat region. Consequently, the radiation dose detecting sensor produces a detected value that is different from the correct value to be detected, and fails to set an appropriate dose of radiation to be applied to the subject.

SUMMARY OF THE INVENTION

It is an object of the present invention to provide a radiation image capturing apparatus which is capable of setting highly accurately an optimum dose of radiation to be applied to an area of interest of a subject, a method of controlling such a radiation image capturing apparatus, an apparatus for and a method of adjusting a radiation dose detector.

A radiation image capturing apparatus according to the present invention comprises a radiation source for applying a radiation to a subject, a radiation image information detector for detecting a radiation from the radiation source which has passed through the subject to capture radiation image information of the subject, a radiation dose detector for detecting a radiation dose which has passed through a region including an area of interest of the subject, means for identifying a region in which a detected value detected from the region including the area of interest by the radiation image information detector is smaller than a predetermined threshold value, as the area of interest, and correcting means for correcting the radiation dose detected by the radiation dose detector based on a detection corrective value calculated from detected values from an entire region including the area of interest and detected values from the area of interest, wherein an exposure control condition for the radiation to be emitted from the radiation source is determined based on the corrected radiation dose.

An apparatus for adjusting a radiation dose detector according to the present invention comprises a radiation image information detector for detecting a radiation which has passed through a subject to capture radiation image information of the subject, a radiation dose detector for detecting a radiation dose which has passed through a region including an area of interest of the subject, means for identifying a region in which a detected value detected from the region including the area of interest by the radiation image information detector is smaller than a predetermined threshold value, as the area of interest, and correcting means for correcting the radiation dose detected by the radiation dose detector based on a detection corrective value calculated from detected values from an entire region including the area of interest and detected values from the area of interest.

A method of controlling a radiation image capturing apparatus according to the present invention comprises the steps of applying a radiation to a subject, detecting, with a radiation image information detector, a radiation from the radiation source which has passed through the subject to capture radiation image information of the subject, detecting, with a radiation dose detector, a radiation dose which has passed through a region including an area of interest of the subject, identifying a region in which a detected value detected from the region including the area of interest by the radiation image information detector is smaller than a predetermined threshold value, as the area of interest, and correcting the radiation dose detected by the radiation dose detector based on a detection corrective value calculated from detected values from an entire region including the area of interest and detected values from the area of interest, wherein an exposure control condition for the radiation to be emitted from the radiation source is determined based on the corrected radiation dose.

A method of adjusting a radiation dose detector according to the present invention comprises the steps of applying a radiation to a subject, detecting, with a radiation image information detector, a radiation from the radiation source which has passed through the subject to capture radiation image information of the subject, detecting, with a radiation dose detector, a radiation dose which has passed through a region including an area of interest of the subject, identifying a region in which a detected value detected from the region including the area of interest by the radiation image information detector is smaller than a predetermined threshold value, as the area of interest, and correcting the radiation dose detected by the radiation dose detector based on a detection corrective value calculated from detected values from an entire region including the area of interest and detected values from the area of interest.

With the radiation image capturing apparatus, the method of controlling the radiation image capturing apparatus, the apparatus for and the method of adjusting the radiation dose detector according to the present invention, the radiation dose detected by the radiation dose detector is corrected into a radiation dose to be applied to the area of interest based on the detected value of the radiation image information detected by the radiation image information detector. Even if the radiation dose detector is not positioned in exact alignment with the area of interest, an appropriate exposure control condition can be determined for the area of interest. Therefore, desired radiation image information of the area of interest can be acquired.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
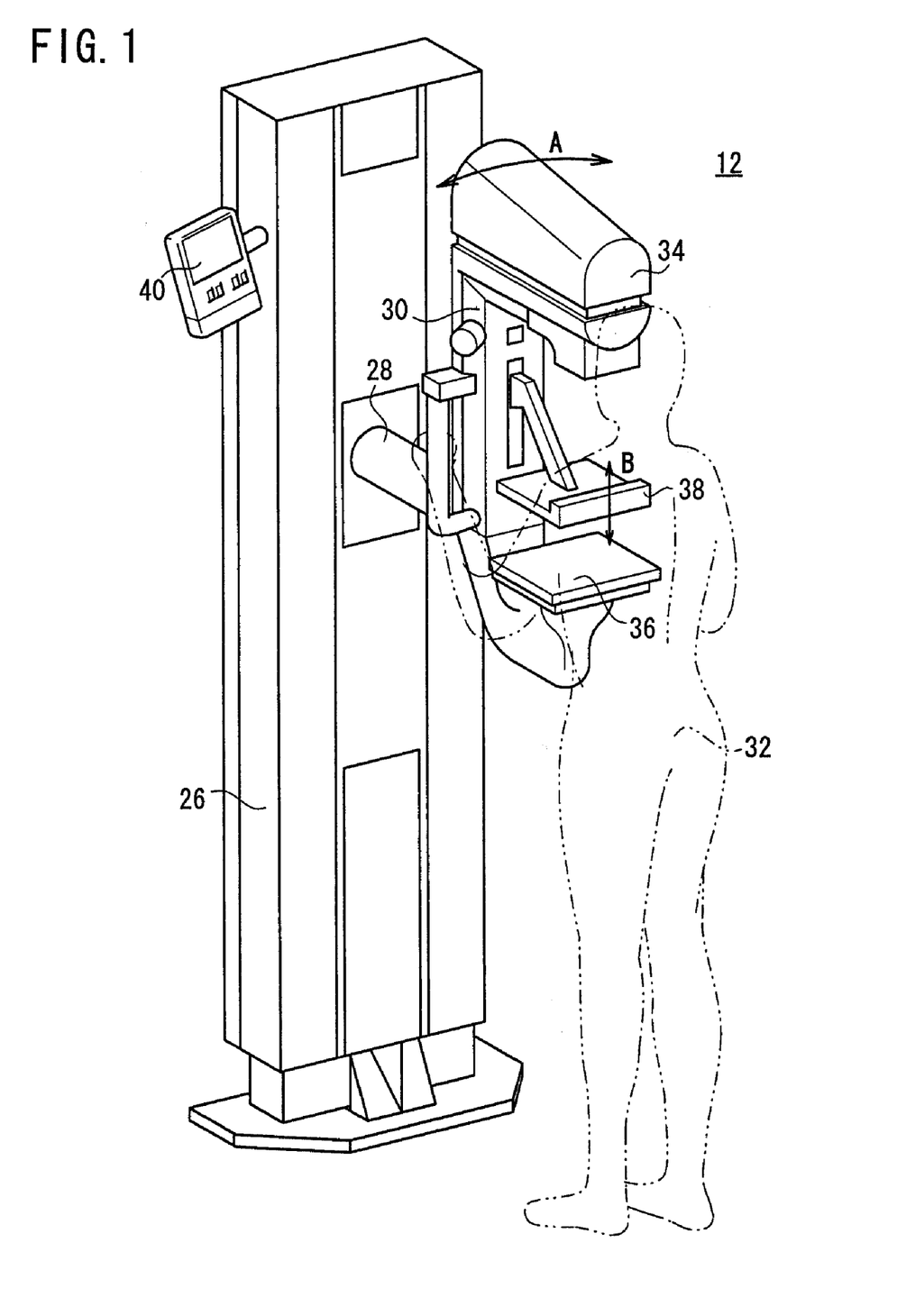
FIG. 1 is a perspective view of a mammographic system according to an embodiment of the present invention.

FIG. 1 shows in perspective a mammographic system 12 to which a radiation image capturing apparatus and a method of controlling the same according to the present invention are applied.

As shown in FIG. 1, the mammographic system 12 includes an upstanding base 26, a vertical arm 30 fixed to a horizontal swing shaft 28 disposed substantially centrally on the base 26, a radiation source housing unit 34 storing a radiation source for applying a radiation to a breast (mammary) 44 (see FIG. 2) to be imaged of a subject 32 and fixed to an upper end of the arm 30, an image capturing base 36 housing a solid-state detector for detecting a radiation that has passed through the breast 44 to acquire radiation image information of the breast 44 and fixed to a lower end of the arm 30, and a presser plate 38 for pressing and holding the breast 44 against the image capturing base 36.

When the arm 30, to which the radiation source housing unit 34 and the image capturing base 36 are secured, is angularly moved about the swing shaft 28 in the directions indicated by the arrow A, an image capturing direction with respect to the breast 44 of the subject 32 is adjusted. The presser plate 38 is connected to the arm 30 and disposed between the radiation source housing unit 34 and the image capturing base 36. The presser plate 38 is vertically displaceable along the arm 30 in the directions indicated by the arrow B.

To the base 26, there is connected a display control panel 40 for displaying image capturing information including an image capturing region, an image capturing direction, etc. of the subject 32 detected by the mammographic system 12, the ID information of the subject 32, etc., and setting these information, if necessary.

Figure 2:
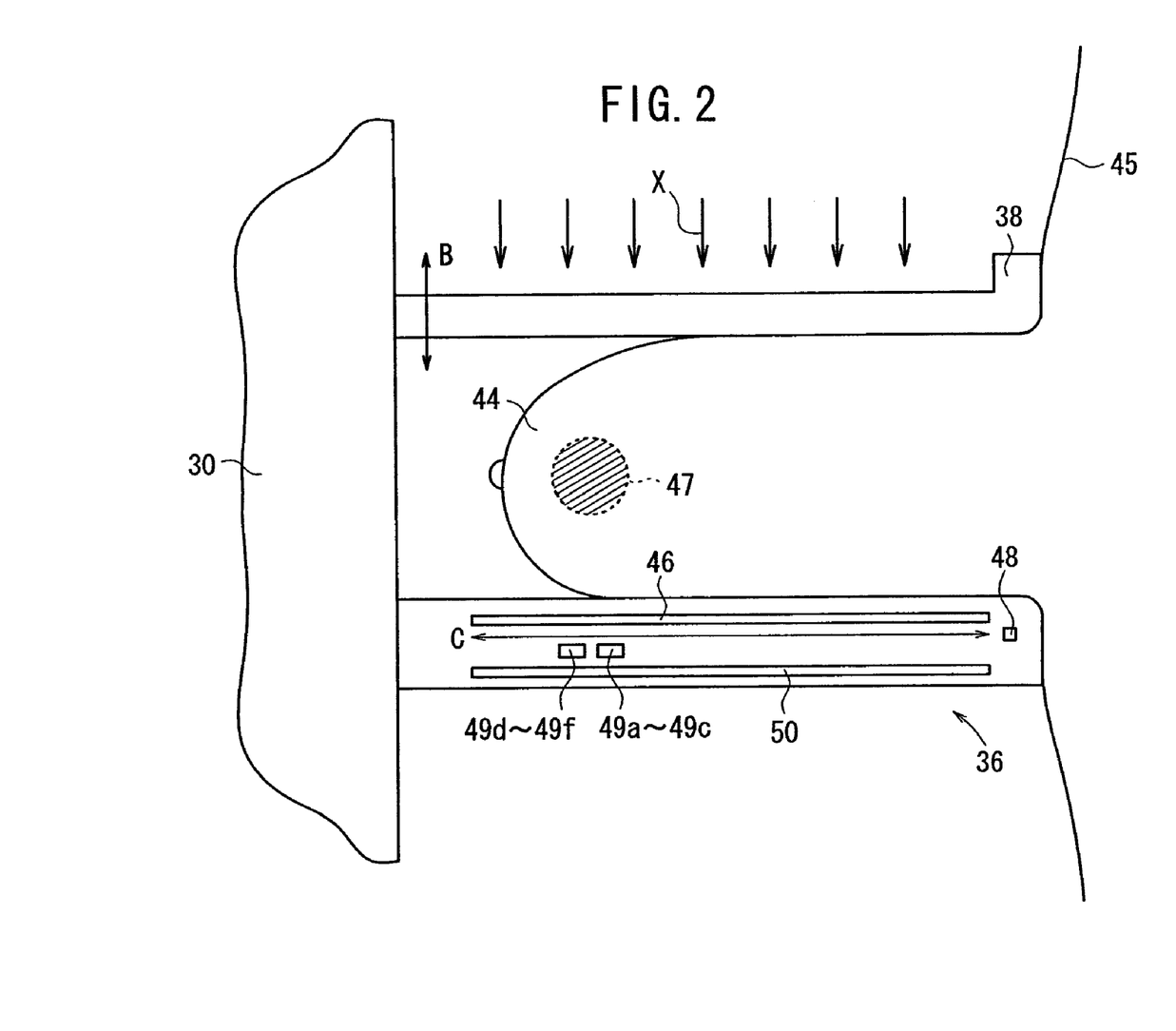
FIG. 2 is a fragmentary vertical elevational view, partly in cross section, showing internal structural details of an image capturing base of the mammographic system according to the embodiment of the present invention.

FIG. 2 shows internal structural details of the image capturing base 36 of the mammographic system 12. In FIG. 2, the breast 44 of the subject 32 is shown as being placed between the image capturing base 36 and the presser plate 38. The reference numeral 45 represents the chest wall of the subject 32.

The image capturing base 36 houses therein a solid-state detector 46 (radiation image information detector) for storing radiation image information based on a radiation X that has been emitted from the radiation source stored in the radiation source housing unit 34 and has passed through the breast 44, and outputting the stored radiation image information as an electric signal, a reading light source 48 for applying reading light to the solid-state detector 46 to read the radiation image information stored in the solid-state detector 46, an automatic exposure control radiation detector (radiation dose detector) (hereinafter referred to as AEC (Automatic Exposure Control) sensors 49a through 49f) for detecting the dose of the radiation X that has passed through the breast 44 and the solid-state detector 46, and an erasing light source 50 for applying erasing light to the solid-state detector 46 to remove unwanted electric charges stored in the solid state detector 46.

The solid-state detector 46 comprises a direct-conversion, light-reading radiation solid-state detector, for example. The solid-state detector 46 stores radiation image information based on the radiation X that has passed through the breast 44 as an electrostatic latent image, and generates an electric current depending on the electrostatic latent image when the solid-state detector 46 is scanned by the reading light applied from the reading light source 48.

The solid-state detector 46 may be a detector as disclosed in Japanese laid-open patent publication No. 2004-154409, for example. More specifically, the solid-state detector 46 comprises a laminated assembly of a first electrically conductive layer disposed on a glass substrate for passing the radiation X therethrough, a recording photoconductive layer for generating electric charges upon exposure to the radiation X, a charge transport layer which acts substantially as an electric insulator with respect to latent image polarity electric charges developed in the first electrically conductive layer and which acts substantially as an electric conductor with respect to transport polarity charges which are of a polarity opposite to the latent image polarity electric charges, a reading photoconductive layer for generating electric charges and making itself electrically conductive upon exposure to the reading light, and a second electrically conductive layer which is permeable to the radiation X. An electric energy storage region is provided in the interface between the recording photoconductive layer and the charge transport layer.

Each of the first electrically conductive layer and the second electrically conductive layer provides an electrode. The electrode provided by the first electrically conductive layer comprises a two-dimensional flat electrode. The electrode provided by the second electrically conductive layer comprises a plurality of linear electrodes spaced at a predetermined pixel pitch for detecting the radiation image information to be recorded as an image signal. The linear electrodes are arranged in an array along a main scanning direction, and extend in an auxiliary scanning direction perpendicular to the main scanning direction.

The reading light source 48 includes, for example, a line light source comprising a linear array of LED chips and an optical system for applying a line of reading light emitted from the line light source to the solid-state detector 46. The linear array of LED chips extends perpendicularly to the direction in which the linear electrodes of the second electrically conductive layer of the solid-state detector 46 extend. The line light source moves along the directions, i.e., the directions indicated by the arrow C, in which the linear electrodes extend to expose and scan the entire surface of the solid-state detector 46.

The erasing light source 50 comprises a plurality of LED chips which can emit and quench light in a short period of time and which have very short persistence, the LED chips being arranged on a panel. Although not shown, the panel extends parallel to the solid-state detector 46 and is housed in the image capturing base 36.

Figure 3:
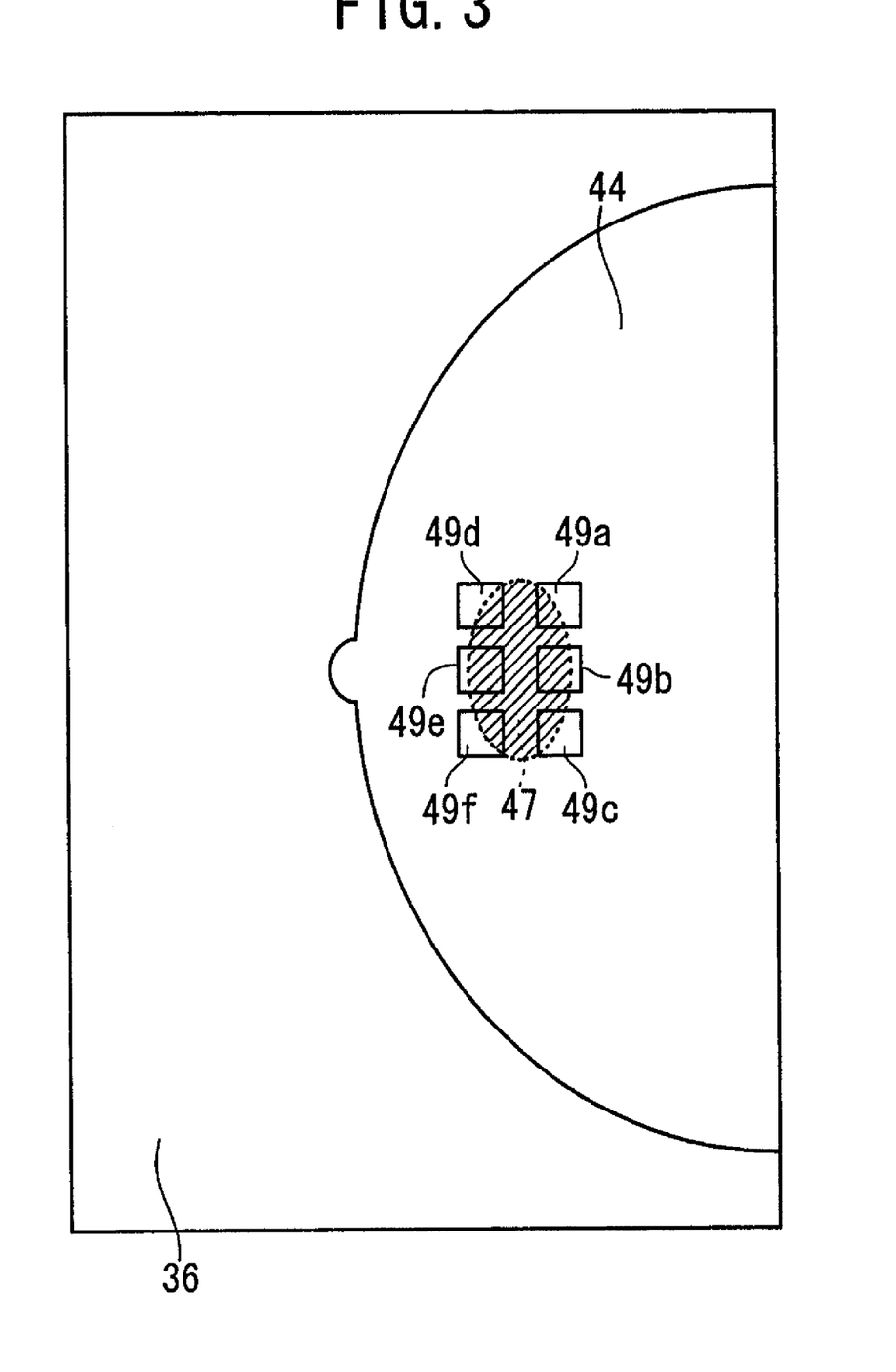
FIG. 3 is a view showing the layout of AEC sensors in the mammographic system according to the embodiment of the present invention.

As shown in FIG. 3, the AEC sensors 49a through 49f are fixedly positioned in a region of the image capturing base 36 where the mammary gland region 47 of the breast 44 is positioned on the image capturing base 36.

Figure 4:
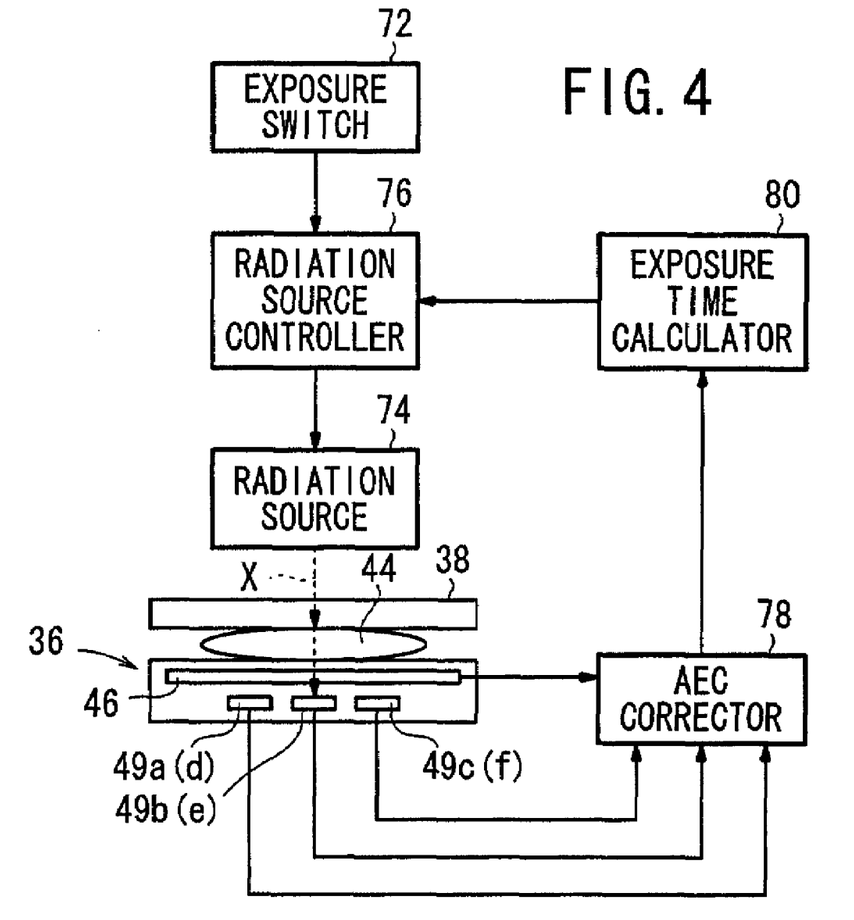
FIG. 4 is a block diagram of a control circuit of the mammographic system according to the embodiment of the present invention.

FIG. 4 is a block diagram of a control circuit of the mammographic system 12.

The control circuit of the mammographic system 12 includes a radiation source controller 76 housed in the radiation source housing unit 34 for controlling a radiation source 74 which emits the radiation X when an exposure switch 72 is operated, an AEC corrector 78 (correcting means) for correcting the dose of radiation detected by the AEC sensors 49a through 49f into a dose of radiation to be applied to the mammary gland region 47 (area of interest), and an exposure time calculator 80 for calculating an appropriate exposure time for the radiation X from the radiation source 74 based on the corrected dose of radiation per time for the mammary gland region 47 and supplying the calculated exposure time as an exposure control condition to the radiation source controller 76.

The mammographic system 12 according to the present embodiment is basically constructed as described above. Operation of the mammographic system 12 will be described below.

Using a console, an ID card, etc., not shown, the operator or radiological technician sets the ID information of the subject 32, an image capturing process, etc. The ID information includes information as to the name, age, sex, etc. of the subject 32, and can be acquired from an ID card owned by the subject 32. If the mammographic system 12 is connected to a network, then the ID information can be acquired from a higher-level apparatus through the network. The image capturing process includes information as to a region to be imaged, an image capturing direction, etc. instructed by the doctor, and can be acquired from a higher-level apparatus through the network or can be entered from the console by the radiological technician. The information can be displayed on the display control panel 40 of the mammographic system 12.

Thereafter, the radiological technician places the mammographic system 12 into a certain state according to the specified image capturing direction. For example, the breast 44 may be imaged as a cranio-caudal view (CC) taken from above, a medio-lateral view (ML) taken outwardly from the center of the chest, or a medio-lateral oblique view (MLO) taken from an oblique view. Depending on information of a selected one of these image capturing directions, the radiological technician turns the arm 30 about the swing shaft 28. In FIG. 1, the mammographic system 12 is set to take a cranio-caudal view (CC) of the breast 44.

Then, the radiological technician positions the breast 44 of the subject 2 with respect to the mammographic system 12. For example, the radiological technician places the breast 44 on the image capturing base 36, and thereafter lowers the presser plate 38 toward the image capturing base 36 to hold the breast 44 between the image capturing base 36 and the presser plate 38, as shown in FIG. 2.

After the above preparatory process is completed, the mammographic system 12 starts to capture an image of the breast 44.

First, the mammographic system 12 operates in a pre-exposure mode in which the dose of the radiation X to be applied to the breast 44 is set to a low level to determine exposure control conditions for the mammary gland region 47. Thereafter, the mammographic system 12 operates in a main exposure mode in which the mammary gland region 47 is irradiated with the dose of the radiation X according to the exposure control conditions determined in the pre-exposure mode. Specific details of the pre-exposure mode and the main exposure mode will be described below.

The radiation source controller 76 controls a tube current to be supplied to the radiation source 22 to set a dose of radiation per unit time to a low level, and applies the low-level dose of radiation X to the mammary 44. As shown in FIG. 3, the AEC sensors 49a through 49f are fixedly positioned in the region of the image capturing base 36 where the mammary gland region 47 of the breast 44 of a standard subject 32 is positioned on the image capturing base 36.

Each of the AEC sensors 49a through 49f detects a dose of the radiation X that has passed through the presser plate 38, the mammary 44, and the solid-state detector 46, and supplies the detected radiation dose to the AEC corrector 78. The AEC corrector 78 calculates a radiation dose Xt per unit time from the dose of the radiation X that is detected in each sampling time by each of the AEC sensors 49a through 49f, and identifies one of the AEC sensors 49a through 49f which has detected the minimum radiation dose Xt.

Specifically, since the mammary gland region 47 less permeable to the radiation X than the other region of the breast 44, the radiation dose Xt detected by one (e.g., the AEC sensor 49b) of the AEC sensors 49a through 49f which has the greatest area covered by the mammary gland region 47 is of a minimum level. Therefore, the AEC sensors 49a through 49f that are covered by the mammary gland region 47 can be identified based on the radiation dose Xt.

Then, a detection corrective value is calculated based on the detected value of the radiation image information acquired from the region of the solid-state detector 46 which corresponds to the region of the radiation detecting surface of the identified one of the AEC sensors 49a through 49f.

Figure 5:
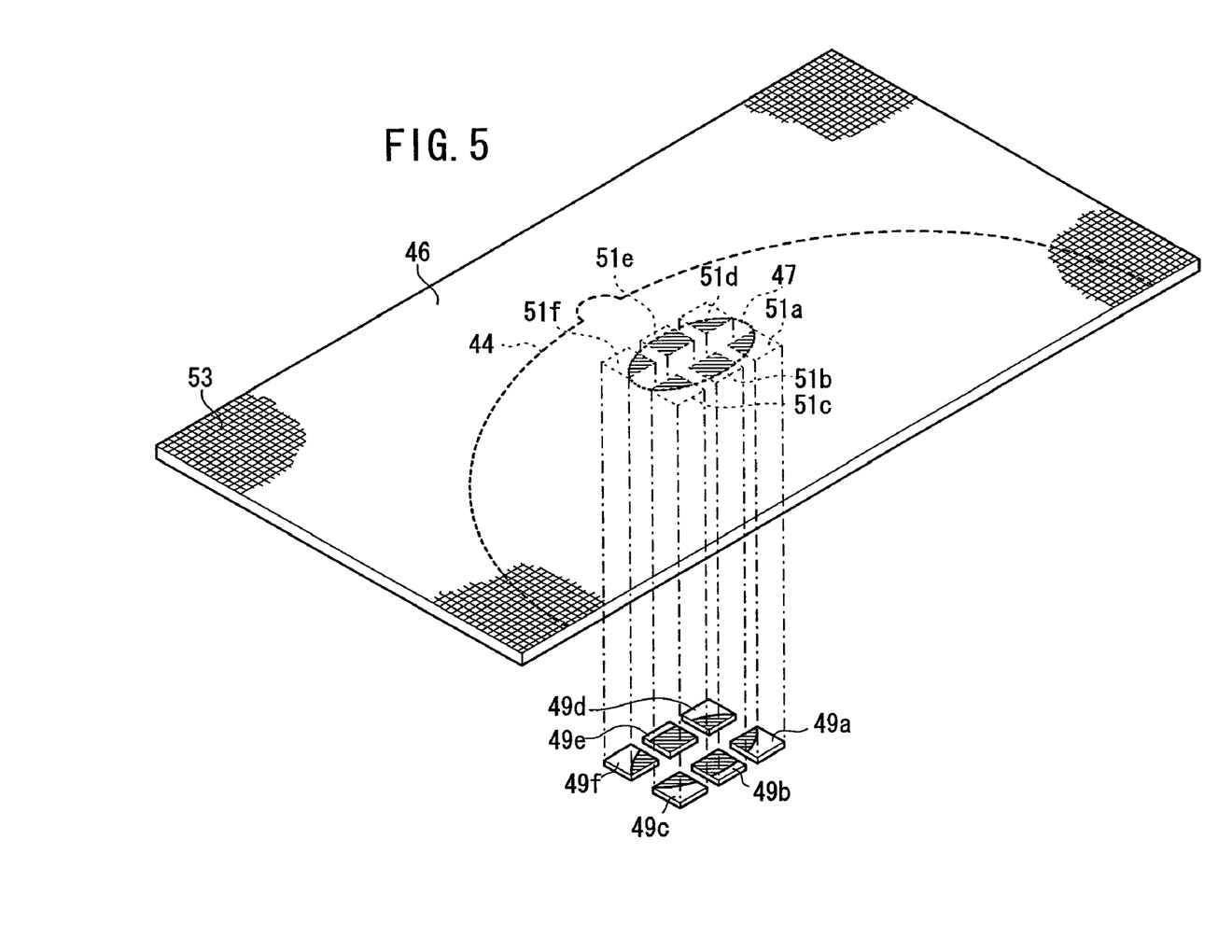
FIG. 5 is a perspective view illustrative of the positional relationship between a solid-state detector and the AEC sensors in the mammographic system according to the embodiment of the present invention.

Specifically, as shown in FIG. 5, the solid-state detector 46 for detecting radiation image information is divided into a number of pixels 53. An average value Te of the detected values from all the pixels that are contained in an identified one of regions 51a through 51f of the solid-state detector 46 which corresponds to the region of the radiation detecting surface of the identified one of the AEC sensors 49a through 49f. Detected values E of radiation image information which are detected by the respective pixels 53 of the identified one of regions 51a through 51f of the solid-state detector 46 are compared with a predetermined threshold value TH which is used to distinguish the mammary gland region 47 from the other region of the breast 44. Then, an average value Le of the detected values E which satisfy the relationship E<TH is calculated.

Figure 6:
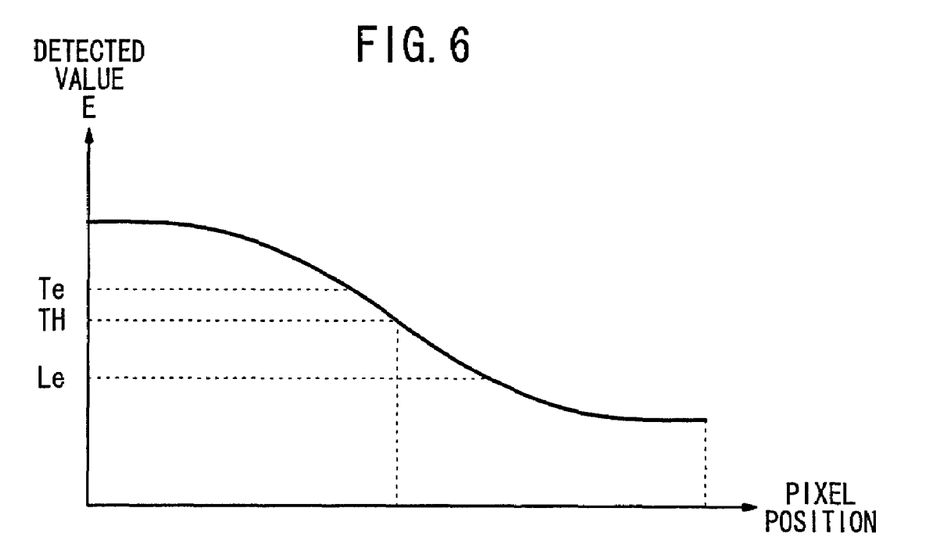
FIG. 6 is a diagram illustrative of the relationship between the detected value from each pixel and a threshold in the mammographic system according to the embodiment of the present invention.

FIG. 6 shows by way of example the relationship between the detected values E detected by the respective pixels 53 of the identified one of regions 51a through 51f of the solid-state detector 46 and the threshold value TH. The AEC corrector 78 calculates a detection corrective value Z for correcting the radiation dose detected by the identified one of the AEC sensors 49a through 49f, from the average value Le and the average value Te, as follows:

$$Z=Te/Le$$

The detection corrective value Z may be calculated from the ratio of the sum of the detected values from all the pixels and the sum of the detected values from the pixels 53 which satisfy the relationship E<TH.

Using the calculated detection corrective value Z, the AEC corrector 78 corrects the radiation dose Xt detected by the identified one of the AEC sensors 49a through 49f to calculate a corrected radiation dose Xt' as follows:

$$Xt'=Xt/Z$$

and outputs the corrected radiation dose Xt' to the exposure time calculator 80. The corrected radiation dose Xt' represents a radiation dose produced when the radiation detecting surface of the identified one of the AEC sensors 49a through 49f is fully covered by the mammary gland region 47.

Based on the corrected radiation dose Xt', the exposure time calculator 80 calculates, as an exposure control condition, an exposure time in which to apply a radiation dose required to obtain appropriate radiation image information of the mammary gland region 47 of the breast 44.

The radiation X applied to the AEC sensors 49a through 49f is partly absorbed by the solid-state detector 46. Therefore, in view of the attenuation of the radiation X caused by the solid-state detector 46, it is necessary to correct the corrected radiation dose Xt' per unit time into a radiation dose per unit time that reaches the detecting surface of the solid-state detector 46. Furthermore, in the pre-exposure mode, since the dose of the radiation X emitted per unit time from the radiation source 74 is set to a low level, it is necessary to correct the radiation dose per unit time that reaches the detecting surface of the solid-state detector 46 in the pre-exposure mode in view of the ratio between the radiation dose emitted per unit time from the radiation source 74 in the pre-exposure mode and the radiation dose emitted per unit time from the radiation source 74 in the main exposure mode.

The exposure time calculator 80 calculates the exposure time in which to apply the radiation X so that a radiation rose required to obtain appropriate radiation image information of the mammary gland region 47 is represented by the product of the radiation dose per unit time on the detecting surface of the solid-state detector 46, which has been corrected in view of the above correcting factors, and the exposure time. The calculated exposure time is set as an exposure control condition in the radiation source controller 76.

Then, inasmuch as certain radiation image information has been recorded in the solid-state detector 46 in the pre-exposure mode, the erasing light source 50 applies erasing light to the solid-state detector 46 to remove the remaining radiation image information from the solid state detector 46 before the main exposure mode starts. Thereafter, the mammographic system 12 starts to operate in the main exposure mode.

In the main exposure mode, the radiation source controller 76 sets the tube current to be supplied to the radiation source 74 to a current level for achieving a radiation dose per unit time that is required in the main exposure mode. Then, when the radiological technician turns on the exposure switch 72, the radiation source 74 emits the radiation X controlled by the tube current to the breast 44 for the exposure time set as the exposure control condition. After the exposure time has elapsed, the radiation source 74 stops applying the radiation X to the breast 44.

During the main exposure mode, the identified one of the AEC sensors 49a through 49f detects the dose of the radiation X, and monitors the radiation dose that is applied until the radiation source 74 stops applying the radiation X to the breast 44. The monitored radiation dose can be used to determine whether the captured radiation image information is acceptable or not. The radiation dose detected by the identified one of the AEC sensors 49a through 49f during the main exposure level may be integrated over time, and if the integrated radiation dose exceeds an allowable level before the exposure time elapses, then the radiation source controller 76 may control the radiation source 74 to stop applying the radiation X. In this manner, the subject 32 is prevented from being exposed to an excessive dose of the radiation X due to a malfunction of the mammographic system 12.

The radiation X that has passed through the breast 44 held between the presser plate 38 and the image capturing base 36 is applied to the solid-state detector 46 housed in the image capturing base 36, by which radiation image information of the breast 44 is recorded. After the radiation image information of the breast 44 is captured, the reading light source 48 moves in the direction indicated by the arrow C (FIG. 2) along the solid-state detector 46 to read the radiation image information recorded in the solid-state detector 46. The radiation image information is supplied to a radiation image forming unit (not shown), which produces a radiation image based on the supplied radiation image information. In order to prepare the solid-state detector 46 to capture a next radiation image, the solid-state detector 46 from which the radiation image information has been read is irradiated with erasing light emitted from the erasing light source 50 to remove unwanted electric charges stored in the solid-state detector 46.

In the illustrated embodiment, the AEC sensors 49a through 49f are fixedly positioned in the region of the image capturing base 36 where the mammary gland region 47 of the breast 44 is positioned on the image capturing base 36. However, the AEC sensors 49a through 49f may be moved in the image capturing base 36. Specifically, the AEC sensors 49a through 49f are moved, and the relative distance that the AEC sensors 49a through 49f are moved with respect to the solid-state detector 46 is calculated by the AEC corrector 78. Based on the calculated distance, the regions 51a through 51f of the solid-state detector 46 which correspond to the respective regions of the radiation detecting surfaces of the AEC sensors 49a through 49f are identified. Then, the detected values E of the radiation image information that are detected by the pixels 53 re compared with the threshold value TH which is used to distinguish the mammary gland region 47 from the other region of the breast 44. If the detected values E are smaller than the threshold value TH, then it is confirmed that the AEC sensors 49a through 49f are moved to a position covered by the mammary gland region 47.

In the illustrated embodiment, one of the six AEC sensors 49a through 49f which has detected the minimum radiation dose Xt per unit time is identified. However, one of the AEC sensors 49a through 49f which has detected a radiation dose Xt that is smaller than the average of radiation doses Xt per unit time which are detected by the AEC sensors 49a through 49f may be identified as an AEC sensor covered by the mammary gland region 47.

Though the six AEC sensors 49a through 49f are employed in the illustrated embodiment, a single AEC sensor may be disposed in a position covered by the mammary gland region 47, and the radiation dose detected by the single AEC sensor and the detected value produced by a region of the detecting surface of the solid-state detector 46 which corresponds to the single AEC sensor may be used. According to such a modification, no AEC sensor needs to be identified in the pre-exposure mode.

Although a certain preferred embodiment of the present invention has been shown and described in detail, it should be understood that various changes and modifications may be made therein without departing from the scope of the appended claims.

What is claimed is:

1. A radiation image capturing apparatus comprising:
   a radiation source for applying a radiation to a subject;
   a radiation image information detector for detecting a radiation from said radiation source which has passed through the subject to capture radiation image information of said subject;
   a radiation dose detector for detecting a radiation dose which has passed through a region including an area of interest of said subject;
   means for identifying a region in which a detected value detected from the region including the area of interest by said radiation image information detector is smaller than a predetermined threshold value, as the area of interest; and
   correcting means for correcting the radiation dose detected by said radiation dose detector based on a detection corrective value calculated from detected values from an entire region including said area of interest and detected values from said area of interest;
   wherein an exposure control condition for the radiation to be emitted from said radiation source is determined based on the corrected radiation dose.

2. A radiation image capturing apparatus according to claim 1, wherein said detection corrective value is calculated based on an average value of the detected values from the entire region including said area of interest and an average value of the detected values from said area of interest.

3. A radiation image capturing apparatus according to claim 1, wherein said radiation dose detector comprises a plurality of radiation dose detectors disposed in respective different positions, and said correcting means compares radiation doses detected respectively by said radiation dose detectors with each other to identify one of said radiation dose detectors which corresponds to said area of interest, and calculates said detection corrective value based on a detected value from a detecting region of said radiation image information detector which corresponds to the position of said identified one of said radiation dose detectors.

4. A radiation image capturing apparatus according to claim 1, further comprising:
   means for calculating the position of said radiation dose detector relative to said radiation image information detector, and identifying said area of interest by comparing a detected value which is detected from the region including said area of interest by said radiation image information detector at said position, with a predetermined threshold value.

5. A radiation image capturing apparatus according to claim 3, further comprising:
   means for calculating the position of said identified one of the radiation dose detectors relative to said radiation image information detector, and identifying said area of interest by comparing a detected value which is detected from the region including said area of interest by said radiation image information detector at said position, with a predetermined threshold value.

6. An apparatus for adjusting a radiation dose detector, comprising:
   a radiation image information detector for detecting a radiation which has passed through a subject to capture radiation image information of said subject;
   a radiation dose detector for detecting a radiation dose which has passed through a region including an area of interest of said subject;
   means for identifying a region in which a detected value detected from the region including the area of interest by said radiation image information detector is smaller than a predetermined threshold value, as the area of interest; and
   correcting means for correcting the radiation dose detected by said radiation dose detector based on a detection corrective value calculated from detected values from an entire region including said area of interest and detected values from said area of interest.

7. An apparatus according to claim 6, wherein said detection corrective value is calculated based on an average value of the detected values from the entire region including said area of interest and an average value of the detected values from said area of interest.

8. An apparatus according to claim 6, wherein said radiation dose detector comprises a plurality of radiation dose detectors disposed in respective different positions, and said correcting means compares radiation doses detected respectively by said radiation dose detectors with each other to identify one of said radiation dose detectors which corresponds to said area of interest, and calculates said detection corrective value based on a detected value from a detecting region of said radiation image information detector which corresponds to the position of said identified one of said radiation dose detectors.

9. An apparatus according to claim 6, further comprising:
means for calculating the position of said radiation dose detector relative to said radiation image information detector, and identifying said area of interest by comparing a detected value which is detected from the region including said area of interest by said radiation image information detector at said position, with a predetermined threshold value.

10. An apparatus according to claim 8, further comprising:
means for calculating the position of said identified one of the radiation dose detectors relative to said radiation image information detector, and identifying said area of interest by comparing a detected value which is detected from the region including said area of interest by said radiation image information detector at said position, with a predetermined threshold value.

11. A method of controlling a radiation image capturing apparatus, comprising the steps of:
applying a radiation to a subject;
detecting, with a radiation image information detector, a radiation from said radiation source which has passed through the subject to capture radiation image information of said subject;
detecting, with a radiation dose detector, a radiation dose which has passed through a region including an area of interest of said subject;
identifying a region in which a detected value detected from the region including the area of interest by said radiation image information detector is smaller than a predetermined threshold value, as the area of interest; and
correcting the radiation dose detected by said radiation dose detector based on a detection corrective value calculated from detected values from an entire region including said area of interest and detected values from said area of interest;
wherein an exposure control condition for the radiation to be emitted from said radiation source is determined based on the corrected radiation dose.

12. A method according to claim 11, wherein said detection corrective value is calculated based on an average value of the detected values from the entire region including said area of interest and an average value of the detected values from said area of interest.

13. A method according to claim 11, wherein said radiation dose detector comprises a plurality of radiation dose detectors disposed in respective different positions, and said step of correcting the radiation dose comprises the steps of:
comparing radiation doses detected respectively by said radiation dose detectors with each other to identify one of said radiation dose detectors which corresponds to said area of interest; and
calculating said detection corrective value based on a detected value from a detecting region of said radiation image information detector which corresponds to the position of said identified one of said radiation dose detectors.

14. A method according to claim 11, wherein said step of identifying a region comprises the steps of:
calculating the position of said radiation dose detector relative to said radiation image information detector; and
identifying said area of interest by comparing a detected value which is detected from the region including said area of interest by said radiation image information detector at said position, with a predetermined threshold value.

15. A method according to claim 13, wherein said step of identifying a region comprises the steps of:
calculating the position of said identified one of the radiation dose detectors relative to said radiation image information detector; and
identifying said area of interest by comparing a detected value which is detected from the region including said area of interest by said radiation image information detector at said position, with a predetermined threshold value.

16. A method of adjusting a radiation dose detector, comprising the steps of:
applying a radiation to a subject;
detecting, with a radiation image information detector, a radiation from said radiation source which has passed through the subject to capture radiation image information of said subject;
detecting, with a radiation dose detector, a radiation dose which has passed through a region including an area of interest of said subject;
identifying a region in which a detected value detected from the region including the area of interest by said radiation image information detector is smaller than a predetermined threshold value, as the area of interest; and
correcting the radiation dose detected by said radiation dose detector based on a detection corrective value calculated from detected values from an entire region including said area of interest and detected values from said area of interest.

17. A method according to claim 16, wherein said detection corrective value is calculated based on an average value of the detected values from the entire region including said area of interest and an average value of the detected values from said area of interest.

18. A method according to claim 16, wherein said radiation dose detector comprises a plurality of radiation dose detectors disposed in respective different positions, and said step of correcting the radiation dose comprises the steps of:
comparing radiation doses detected respectively by said radiation dose detectors with each other to identify one of said radiation dose detectors which corresponds to said area of interest; and
calculating said detection corrective value based on a detected value from a detecting region of said radiation image information detector which corresponds to the position of said identified one of said radiation dose detectors.

19. A method according to claim 16, wherein said step of identifying a region comprises the steps of:
calculating the position of said radiation dose detector relative to said radiation image information detector; and
identifying said area of interest by comparing a detected value which is detected from the region including said area of interest by said radiation image information detector at said position, with a predetermined threshold value.

20. A method according to claim 18, wherein said step of identifying a region comprises the steps of:

calculating the position of said identified one of the radiation dose detectors relative to said radiation image information detector; and identifying said area of interest by comparing a detected value which is detected from the region including said area of interest by said radiation image information detector at said position, with a predetermined threshold value.

* * * * *